United States Patent
Giuliano et al.

(10) Patent No.: US 7,989,007 B2
(45) Date of Patent: Aug. 2, 2011

(54) WEIGHT LOSS COMPOSITION

(75) Inventors: Vincent Giuliano, Winter Springs, FL (US); James Manley, Winter Springs, FL (US)

(73) Assignee: Vincent James Enterprises, LLC, Winter Springs, FL (US)

( * ) Notice: Subject to any disclaimer, the term of this patent is extended or adjusted under 35 U.S.C. 154(b) by 271 days.

(21) Appl. No.: 12/120,223

(22) Filed: May 13, 2008

(65) Prior Publication Data

US 2009/0214680 A1 Aug. 27, 2009

Related U.S. Application Data

(60) Provisional application No. 60/929,588, filed on Jul. 3, 2007.

(51) Int. Cl.
| | |
|---|---|
| A61K 36/00 | (2006.01) |
| A61K 31/137 | (2006.01) |
| A61K 36/25 | (2006.01) |
| A61K 36/254 | (2006.01) |
| A61K 36/258 | (2006.01) |
| A61K 36/752 | (2006.01) |
| A61K 36/48 | (2006.01) |
| A61K 31/44 | (2006.01) |

(52) U.S. Cl. ........ 424/725; 424/728; 424/729; 424/736; 424/757; 514/356

(58) Field of Classification Search .................. None
See application file for complete search history.

(56) References Cited

U.S. PATENT DOCUMENTS

| | | | |
|---|---|---|---|
| 4,223,023 A | 9/1980 | Furda | |
| 4,491,578 A | 1/1985 | Peikin | |
| 4,833,128 A | 5/1989 | Solomon et al. | |
| 5,587,190 A | 12/1996 | Guezennec et al. | |
| 5,726,146 A | 3/1998 | Almada et al. | |
| 5,925,377 A * | 7/1999 | Gerth et al. | 424/451 |
| 5,932,561 A | 8/1999 | Meyers et al. | |
| 5,980,968 A | 11/1999 | Booth | |
| 6,541,026 B2 | 4/2003 | Siskind | |
| 6,706,697 B1 | 3/2004 | MacDonald | |
| 6,797,290 B2 | 9/2004 | Dartey et al. | |
| 6,899,892 B2 | 5/2005 | Gallaher et al. | |
| 7,037,531 B2 | 5/2006 | King et al. | |
| 7,214,778 B2 * | 5/2007 | Zhuang et al. | 530/395 |
| 2002/0019334 A1 | 2/2002 | Portman | |
| 2002/0136782 A1 | 9/2002 | Fleischner | |
| 2004/0001817 A1* | 1/2004 | Giampapa | 424/94.1 |
| 2004/0005368 A1 | 1/2004 | Mann et al. | |
| 2005/0260285 A1* | 11/2005 | DiMateeo-Leggio | 424/725 |
| 2006/0078627 A1 | 4/2006 | Maletto et al. | |
| 2006/0240125 A1 | 10/2006 | Astrup et al. | |
| 2006/0257497 A1* | 11/2006 | Bartels-Arntz et al. | 424/535 |
| 2006/0275513 A1 | 12/2006 | Gardiner et al. | |
| 2007/0014878 A1 | 1/2007 | Gardiner et al. | |
| 2007/0021506 A1 | 1/2007 | Smriga et al. | |
| 2007/0031568 A1 | 2/2007 | Gardiner et al. | |

FOREIGN PATENT DOCUMENTS

| | | |
|---|---|---|
| JP | 3-280855 | 12/1991 |
| JP | 3280855 A2 | 12/1991 |
| JP | 5-192090 | 8/1993 |
| JP | 5192090 A | 8/1993 |
| WO | WO 2004/002241 A1 * | 1/2004 |
| WO | WO 2007/064208 A1 * | 6/2007 |

OTHER PUBLICATIONS

"Daily Biobasics Triple Protein Shake," http://lifeplusvitamins.com/supershake.html, 10 pages printed from the Internet on Mar. 15, 2007.
"Could Micronutrients be the Future of Diet Design?", http://www.foodnavigator.com/news/ng.asp?id=68031-1-leucine-weight-loss-diets, 4 pages printed from the Internet on Mar. 15, 2007.
"Healthful Beverages to Watch in 2007," http://bevindustry.com/content.php?s=BI/2007/02&p=8, 4 pages printed from the Internet on Mar. 15, 2007.
"Healthful Beverages to Watch in 2007," Beverage Industry, http://bevindustry.com/scommon/print.php?s=BI/2007/02&p=8, accessed on Apr. 6, 2008.
Stephen Daniells, "Could micronutrients be the future of diet design?," FoodNavigator.com, May 30, 2006, http://www.foodnavigator.com/news/printNewsBis.asp?id=68031, accessed on Apr. 6, 2008.
"The Amazing Ultimate High Protein, Low Carb, Low Fat, Weight Loss Diet Nutrition Shakel," http://lifeplusvitamins.com/supershake.html, accessed on Apr. 6, 2008.

* cited by examiner

*Primary Examiner* — Qiuwen Mi
(74) *Attorney, Agent, or Firm* — Robert Plotkin, P.C.

(57) ABSTRACT

The present invention comprises a purposefully formulated weight loss composition and a method for causing a meaningful weight loss in a living human subject. The formulated weight loss composition, in its most preferred embodiments comprises: at least one amino acid that is a pharmacologically active precursor in the catecholamine biosynthesis pathway; one or more sympathomimetic agents; a lipolytic agent; a high-Dalton macromolecular protein, and a plurality of micronutrients. The preferred composition is formulated as a dry particulate admixture initially; and then is made into a fluid beverage, which is able to achieve multiple physiologic functions in-vivo. These in-vivo functions include: causing a meaningful weight loss, with a preference for lipolysis and fat metabolism; providing for a low glycemic index; offering lean muscle maintenance and replenishment; and concomitantly initiating dopaminergic (D2-receptor) brain stimulation, resulting in improved cognitive function and affective augmentation.

7 Claims, No Drawings

WEIGHT LOSS COMPOSITION

CROSS REFERENCE TO RELATED APPLICATIONS

This application claims priority from U.S. Provisional Patent Application Ser. No. 60/929,588, filed on Jul. 3, 2007, entitled "Weight Loss Composition," which is hereby expressly incorporated by reference.

FIELD OF THE INVENTION

The present invention is directed to an unique weight loss composition which is suitable for ingestion by an obese person and has been formulated to induce a marked increase in the person's basal metabolism rate. More precisely, the present invention concerns a dry particle admixture that is prepared in advance and is subsequently converted on-demand into a fluid beverage before being swallowed and consumed by humans. The fluid beverage is specifically formulated to promote weight loss in obese persons by inducing an enhanced basal metabolic rate in the individual; preferentially metabolizes fats and oxidizes fatty acids stored in the body; and augments muscle breakdown as well as provides for muscle replenishment. The formulated beverage is also able to produce a low glycemic index for diabetics and the like; and can augment cognitive function via dopaminergic (D2-receptor) stimulation.

BACKGROUND

Obesity as a Disorder

Obesity is an increasingly common clinical disorder and pathology in both highly developed and newly emerging countries. Over 300 million adults are deemed to be clinically obese worldwide, according to the latest statistics from the World Health Organization and the International Obesity Task Force [Belza et al., Int. J. Obesity, 2007, 31, 121-130.] Moreover, about one-quarter of the entire U.S. adult population is today considered to be obese; and the rates for obesity in Western Europe are also very much on the rise, although not yet at the incidence rate presently existing in the U.S. There is also substantial clinical and epidemiological evidence accumulated to date that reveals that obesity now represents an additional independent risk factor for the development of both cardiovascular disease and hypertension [Rashid et al., Prev. Cardiol., 2003, 38, 19-36].

By common medical definition, a person is traditionally considered to be obese if the individual is more than 20% over his ideal weight. The ideal weight takes into account the person's weight, age, sex and build.

The National Institutes of Health offers a more precise definition of obesity as a body mass index (or "BMI") of 30 and above. The BMI is a mathematically calculated index for relating body weight to height; and is determined as a person's weight (in kilograms) divided by his height (in meters squared). For this reason, the BMI correlates strongly in adults with the total body fat content; and a person having a BMI of 30 is typically about 30 pounds overweight.

Metabolic Factors Associated with Obesity

Although many of the controlling factors associated with obesity still remain poorly recognized today, two medical conditions in particular have become associated with and largely implicated in the pathogenesis of obesity (i.e., the development of those morbid conditions typifying obesity as a disease state, and more specifically the biochemical and physiological mechanism by which obesity as a disease progresses). These two medical conditions are: (1) a demonstrable increase in the activity of the sympathetic nervous system; and (2) the occurrence of hyperinsulinemia—i.e., the presence of an excessive and inappropriate amount of insulin in the blood—usually as a secondary consequence to insulin resistance [Parker et al., Diabetes Care, 2002, 25, 425-430].

It has long been recognized that the sympathetic nervous system, a division of the autonomic nervous system, plays an important role in the normal and routine regulation of energy intake and energy expenditure in-vivo. Among its multiple recognized effects, a stimulation of particular sympathetic nerves will produce responses that facilitate increased muscle activity; cause vasodilation of the blood vessels of skeletal and cardiac muscles; and induce activation of adenyl cyclase, an enzyme necessary to promote the breakdown of glycogen into glucose in the liver.

Also, an increase in sympathetic nerve activity can itself counteract the recognized detrimental effects of hyperinsulinemia because catecholamines (a distinct chemical class of biologically active compounds such as dopamine, norepinephrine and epinephrine) not only serve as direct stimulators of the sympathetic nervous system, but are also recognized as being substances able to initiate fat oxidation. The likelihood of an increase in sympathetic nervous system activity also causing an increase in fat oxidation is further supported by the existence of a positive correlation between a resting heart rate and the rate of basal fat oxidation [Nuttall et al., J. Clin. Endocrinol. Metab., 2003, 88, 3577-3583].

The Basal Metabolic Rate

The basal metabolic rate (or "BMR") is the rate of energy exchange in resting living subjects and reflects the energy requirements of those cellular and tissue processes associated with the vital activities for that person when in a true resting state. The individual's basal metabolic rate is a controlling factor of oxidative metabolism in the human body; and this rate will affect the net balance between a person's caloric intake and his actual energy consumption. Thus, if a person's caloric intake is being controlled as a fixed caloric amount ingested per day, then the rate of his energy consumption becomes the determining factor for his rate of basal metabolism.

This essential principle concerns all those persons who are considered to be obese. Perhaps the most significant clinical finding for such obese persons is that they routinely show a much slower basal metabolic rate when compared to their non-obese counterparts. Many clinical studies have therefore suggested that these slower rates of basal metabolism in an obese person are directly related to the significant differences in total body fat content which exists between obese persons and their non-obese counterparts [Belza et al., Int. J. Obesity, 2007, 31, 121-130.]

The value and importance of having a higher rate of basal metabolism, which results in a higher energy expenditure and thereby avoids adding to the body weight, is illustrated by the published medical studies which collectively reveal that there is a significantly lower basal metabolic rate in human subjects medicated with β-blockers, such as atenolol [Hirsch et al., Obes. Res., 2000, 8, 227-233]. This data and evidence is entirely consistent with other published reports that β-adrenergic blockade directly affects the person's energy expenditure by lowering the basal metabolic rate [Hirsch et al., Obes. Res., 2000, 8, 227-233]. For example, the Prospective Diabetes Study [Lindholm et al., Lancet, 2002, 359, 1004-1010] reports that living subjects being treated for hypertension with atenolol (a β-adrenergic blockade drug) showed twice the weight gain compared to other hypertension patients being treated with captopril (a specific competitive inhibitor of angiotensin I-converting enzyme or "ACE", the enzyme responsible for the conversion of angiotensin I to angiotensin II), despite each drug achieving very similar degrees of hypertension control for the subject.

Preferential Sources of Energy in the Body

Whenever a need for more energy exists in a living human subject, the energy producing pathways of the body preferentially metabolize those kinds of food that most efficiently serve as a source of glucose. Glucose (or dextrose) is a simple six-carbon sugar and is the chemical compound most preferred and easiest accessed as an energy source to maintain basic physiologic functions and homeostasis for the body. However, in the absence of having glucose (or dextrose) available as a direct energy source, the biochemical energy producing pathways in the living body will seek out other available kinds of food as preferred energy sources.

For this purpose and reason, carbohydrates are the substances first chosen and most preferably selected by the body as a glucose source. Nevertheless, carbohydrates as such are not stored within the body tissues; and therefore must be regularly ingested as food in order to provide the energy producing pathways with sufficient quantities of substrate for metabolism and energy production.

However, if carbohydrates are not available within the body for any reason, the second best food source then preferably selected is protein. As a distinct chemical class, proteins can be metabolized by the body into energy, but such protein metabolism proceeds in a biochemical manner and via a series of biochemical pathways that are far less efficient than with carbohydrates. For these reasons, when glucose and carbohydrates are not ingested in any substantial quantity and thus are routinely absent from the diet for any cause, the energy producing pathways in the human body will then preferably metabolize proteins rather than fat, because proteins are easier to utilize as a source for the generation of energy than fat.

Yet, if and when proteins are in fact metabolized by the body as an energy source over any substantial duration of time, the consequences of this event are adverse. Typically, a major breakdown and destruction of the skeletal muscles occurs—primarily because the muscles are the sites in the body where protein is stored in bulk; and this event in turn routinely causes a pathological condition of serious "muscle wasting" in the body, as well as concomitantly creates a markedly increased creatinine production overload for the kidneys to eliminate. Neither consequence of protein metabolism is desirable.

Fats and fatty acids are the third and least desirable food able to be metabolized by the body as a source of energy, primarily because they are biochemically oxidized in the slowest and least efficient manner. Clearly, for obese persons, a decided preference by the energy producing pathways of the body for fat metabolism (over proteins and carbohydrates) would be most desirable; nevertheless, creating such a preference for fat metabolism appears to be most difficult to achieve.

Conventional Methods for Inducing a Weight Loss

Despite all the existing research and development performed to date, there appear to be a very limited number of ways to generate a meaningful weight loss for an obese human. The conventional choices employed to date are summarily reviewed below.

Medicaments and Pharmaceuticals

Pharmaceuticals and medicaments represent one conventionally available means by which to achieve a weight loss for some obese persons. However, the range of presently available pharmacologically effective compositions is extremely limited; they are frequently quite expensive; and they exhibit many undesirable side effects. Representative examples of FDA-approved orally-prescribed medications, available by prescription, include phentermine, subutramine, and orlistat.

Phentermine is one of the older appetite-suppressing drugs approved by the FDA in 1959, with a mechanism of action similar to the stimulant, amphetamine, and therefore is classified as a Class IV controlled drug. Phentermine is a centrally-acting stimulant which increases catecholamine activity, triggering appetite suppression. The pharmacologic effects are generally well-tolerated, but associated with significant potential for physical and psychological dependence [Nelson et al., Endocrine, 2006, 29, 49-60.]

Sibutramine (under the trade names Meridia® in the U.S. and Reductil® in the E.U.), is a centrally-acting serotonin-norepinephrine reuptake inhibitor structurally similar to amphetamine. Sibutramine increases serotonergic action, which is thought to suppress appetite, but is associated with a significant side effect profile and potential drug interactions; in particular, monoamine oxidase inhibitors (MAOIs), which can cause 'serotonin syndrome,' a rare and serious adverse drug reaction. Other side effects include increase in blood pressure, heart rate, and cardiac arrhythmias [Portyansky et al., Drug Topics, 1998, 142, 23.]

Orlistat (marketed in the U.S. under the trade name Xenical® and tetrahydrolipstatin in the E.U.) inhibits the action pancreatic lipase on triglycerides in the intestine, preventing the absorption of fats in the human diet, and thereby reducing caloric intake. The drug is associated with significant gastrointestinal side effects, such as steatorrhea, fecal incontinence, and excessive flatulence [Zhi et al., J. Clin. Pharmacol., 1995, 35, 1103-1108.] Long-term side effects include a link between orlistat and aberrant crypt foci, lesions found in the colon, believed to be an early precursor of colon cancer [Garcia et al., Cancer Lett., 2006, 240, 221-224.]

Exercise and Physical Fitness Programs

Physical exercise is a second conventional technique for achieving weight loss. The benefits of physical exercise and its capability for causing a loss of weight are today now so publicly advertised that no serious doubt exists as to their value or effectiveness. However, despite the many different excise programs and fitness regimens publicly offered today, very few obese persons seem to find sufficient motivation, or adequate determination, or enough physical endurance to continue such exercise programs for any meaningful length of time.

Controlled Caloric Count and Food Type Diets

A third general approach is to decrease the amount of caloric consumption per day—i.e., a controlled caloric count diet. Although the range and variety of such dieting programs is large and has long been a popular fad, most utilize one of two different techniques: directly decreasing the amount of food and limiting the total calories ingested to a fixed quantity per day; and controlling which kinds of foods or food groupings are eaten in order to trick the metabolic mechanisms and energy producing pathways of the body.

The essence of the former technique is to replace high calorie foods with substitute lower calorie foods. The process of weight loss in this manner requires considerable attention, time and effort as well as a prolonged and unchanging caloric restriction in order to be effective; and the regimen must frequently be accompanied by significant changes of personal lifestyle or by major life management modifications to obtain truly meaningful and lasting results.

In comparison, the essence of the latter technique is that the foods and food groups are divided into specific categories such as carbohydrates, proteins, and fat; and certain types/kinds of food are to be entirely avoided, while others must be consumed in relatively high quantities. Thus, some regimens restrict the calorie intake by purposely eliminating all carbohydrates from the person's diet, and substituting huge quantities of proteins. This approach has become known as the high-protein (and low-carbohydrate) diet; and has been popularized in many widely used variant formats.

Most of these substitute dietary foods contain proteins in large percentage quantities; and typically are powdered admixtures containing soy, whey, or casein (milk) proteins. However, many typical high protein dietary products are not miscible with water; and consequently must take the form of solid bars, thick-liquids, or suspensions that are to be orally consumed by the person together with copious amounts of water or other aqueous based liquids.

Another commonly encountered feature of this dietary regimen is the relatively high caloric content of these substitute high protein foods. Once eaten, the higher caloric content of proteins will typically increase the glycemic index within the person's bloodstream—i.e., generate very high concentrations of glucose in the blood, a medical condition which is nether healthy nor beneficial for any person in general, and one which is particularly hazardous and adverse for those persons having medical problems related to glucose intolerance, insulin resistance, or diabetes.

Finally, for many individuals, the substitute high protein foods are not readily bioabsorbable from the digestive tract and are often difficult to metabolize. Also, a usual byproduct or waste product of protein metabolism is creatinine, which under normal conditions is routinely eliminated from the body by the kidneys. Nevertheless, as a direct consequence of consuming a high protein diet, a major and prolonged increase of creatinine production will inevitably occur; and this greater volume of creatinine must still be removed and eliminated by the kidneys. Over time, the increase of creatinine production can result in severe renal dysfunction and cause permanent damage to the kidneys.

Dietary Supplements to Induce Satiety

A related, but distinctly different, approach has been to use nutritional intervention compositions which are taken prior to a meal in order to produce a feeling of satiety before the meal, and/or to extend the period of satiety following consumption of a meal in order to lengthen the time interval between one meal and the next. The nature and constituents typical of such nutritional intervention compositions are represented by the following examples.

U.S. Pat. No. 4,491,578 describes the oral administration of a trypsin inhibitor to enhance satiety. This technique relies upon an in-vivo secretion and release of cholecystokinin (or "CCK") as a negative feedback signal, which is caused by a release of trysin from the pancreas. The purposeful administration of the trypsin inhibitor blocks the release of trypsin from the pancreas, thereby interfering with the negative feedback mechanism.

U.S. Pat. No. 4,833,128 discloses the oral administration of phenylalanine in conjunction with protein, carbohydrate and fat to stimulate satiety. When this dietary supplement is consumed fifteen minutes before a meal, a feeling of satiety is generated which causes that person to eat less food during the meal.

U.S. Pat. No. 5,932,561 reveals that dietary supplements that bind lipids can aid in weight loss and reduce cholesterol levels in the body. It also teaches that dietary supplements that contain saponins from aloe (saponins being any of a group of varied triterpene or steriod glycosides occurring in many plants including aloe) will increase the capacity of chitosan (partially or fully deacetylated chitin) to bind fat.

U.S. Patent Publication No. 2002/0019334 A1 discloses a dry powder composition for enhancing satiety prior to a meal and extending satiety after a meal in a calorically efficient fashion. The nutritional composition includes protein, caseinmacropeptide or glycomacropeptide, long chain fatty acids, soluble and/or insoluble fibers; and may also include plant saponins, calcium and cholestyramine.

U.S. Pat. No. 6,797,290 describes a composition for appetite control in a human or animal. The composition comprises both chitosan and glycomacropeptide (GMP), wherein the chitosan and glycomacropeptide are present in other than a cationic gum or a polysaccharide/protein complex.

Supplements Formulated to Achieve Other Goals

A diverse range and variety of formulated supplements have also been proposed and developed to achieve other goals and specified purposes which are not concerned with causing a meaningful weight loss for obese persons. It is possible however, that these developments will be incidentally associated with or wrongly confused with effective dietary means for inducing a meaningful weight loss in obese persons. To avoid such misunderstandings, a summary listing of such peripheral developments is given here.

U.S. Pat. No. 4,223,023 describes the use of chitosan as a food additive or as a pharmaceutical preparation to reduce the absorption of lipids in-vivo. The chitosan, as such or in the form of a fatty acid complex, may be admixed with food in a minor quantity in an amount of about 1-10 percent by weight; may be incorporated in a pharmaceutical preparation or composition for oral administration in an amount sufficient to reduce lipid absorption.

U.S. Pat. No. 5,587,190 reveals a composition intended to be absorbed before, during, and after an energy utilizing physical activity; and which allows the activity to be sustained by limiting the effects due to depletion of the available reserves of glycogen in the individual. The composition to be absorbed comprises carbohydrates and lipids; and the lipid fraction must constitute 10-55% of the total calorie content in the composition.

U.S. Pat. No. 5,726,146 presents a dietary supplemental formulation which increases lean body mass without a concomitant increase of body fat mass. The formulated composition comprises creatine, taurine, ribonucleic acid; and optionally includes a carbohydrate (such as starch or a simple saccharide) for enhancing cellular uptake. The formulated composition may be taken alone or in combination with a nutrient base (e.g., proteins, carbohydrates, vitamins, minerals, and other amino acids).

U.S. Pat. No. 5,980,968 offers a controlled-release formula for use as performance drinks, sport drinks, electrolyte drinks, and the like. The controlled release formula composition comprises at least one carbohydrate; and at least two different biodegradable polymers selected from particular chemical compounds having a specified range of molecular weights.

U.S. Pat. No. 6,706,697 describes a diabetic nutritional and weight loss drink powder composition useful for maintaining proper nutritional and weight management in diabetic persons, while controlling and stabilizing their blood sugar levels. The diabetic nutritional and weight loss composition comprises a major amount of isolated soy protein, milk protein isolate, and fructose; a minor amount of inulin, guar gum, potassium chloride, microcrystalline cellulose, and flavoring; and a minute amount of vitamins, minerals, and other incidental ingredients.

U.S. Pat. No. 7,037,531 reveals a chewable or edible energy bar which will provide a source of energy when there is a need for a short term energy supply, such as during physical exercise or in certain aerobic and anaerobic energy depleting conditions. The energy bar is formulated as a multi-saccharide food product; and includes a saccharide component of 5-20% galactose, 0-25% creatine, and optionally further ingredients selected from carbohydrate, fibre, and fat.

U.S. Patent Publication No. 2006/0275513 A1 discloses a diet supplement comprising at least Green Tea Extract and Oolong Tea Extract, and which alternatively also includes anhydrous caffeine. This diet supplement is said to used as a time-release mechanism for sustained all-day energy, the burning of calories, supporting weight loss, and improving mental focus.

U.S. Patent Publication No. 2007/0014878 A1 reveals compositions and methods increasing a person's natural metabolic rate, for increasing thermogenesis, for increasing training intensity, for increasing muscular definition, and for decreasing water retention in a human being. The compositions comprise green tea extract, anhydrous caffeine, theobroma cacao extract, oolong tea extract, white tea extract, guarana, yerba mate powder, dandelion root extract, juniper berry powder, parsley powder garncinia cambogia extract, cayenne pepper powder extract, n-acetyl-1-tyrosine, quercetin dehydrate, gynostemma pentaphyllum extract, vinpocetine; and optionally thiamin, pyridoxine, picamilone, xanthinol nicotinate, garcinia camborgia extract, and niacin.

U.S. Patent Publication No. 2007/00315668 A1 describes a dietary supplement and method for increasing energy and mental alertness in a human or animal subject. The supplement comprises at least Anhydrous Caffeine, Taurine, an extract of American Ginseng Root, and an extract of Green Tea leaf and tender shoots.

U.S. Patent Publication No. 2007/0021506 A1 describes a composition for relieving stress and/or disorders caused by stress. This composition comprises lysine and arginine as active ingredients, which may be provided in the form of a salt. The kinds of stress to be relieved using this composition include mental strain, repetitive work, intellectual labor, menopausal mental instability, anxiety and strain with respect to a future event, and premenstrual mental instability and strain.

Despite all the foregoing, an effective combination of nutritional ingredients, which addresses all of the various medical concerns and considerations and is directed specifically to inducing a meaningful weight loss in obese persons has not yet been found to date. Thus, a weight loss composition which is effective for use with obese persons and solves the aforementioned problems would be seen today as an unique and unforeseen development in the technical field.

SUMMARY

The instant invention has multiple aspects and alternative definitions.

A first aspect of the present invention provides a dry weight loss composition suitable for ingestion by obese persons and comprises a particle admixture of: at least one exogenous amino acid precursor able to be utilized in a catecholamine biosynthesis pathway; at least one exogenous sympathomimetic agent able to stimulate the sympathetic nervous system; and at least one substance selected from the group consisting of a lipolytic agent and a high-Dalton macromolecular protein.

A second aspect of the present invention offers a fluid weight loss composition suitable for ingestion by obese persons and comprises: at least one exogenous amino acid precursor able to be utilized in a catecholamine biosynthesis pathway; at least one exogenous sympathomimetic agent able to stimulate the sympathetic nervous system; at least one substance selected from the group consisting of a lipolytic agent and a high-Dalton macromolecular protein; and a liquid aqueous carrier.

A third aspect of the instant invention provides a method for producing a measurable weight loss in a living obese subject, said method comprising the steps of:
    obtaining a fluid weight loss composition comprising:
    (i) at least one exogenous amino acid precursor able to be utilized in a catecholamine biosynthesis pathway,
    (ii) at least one exogenous sympathomimetic agent able to stimulate the sympathetic nervous system,
    (iii) at least one substance selected from the group consisting of a lipolytic agent and a high-Dalton macromolecular protein, and
    (iv) a liquid aqueous carrier;
orally administrating said fluid weight loss composition to the living individual subject on a scheduled basis and in predetermined dose quantities over a decided duration of time;
    allowing the orally administered fluid weight loss composition to induce a marked increase in the basal metabolic rate for the living individual subject over time; and
    permitting said induced increase in the basal metabolic rate to cause a measurable weight loss for the living individual subject.

DETAILED DESCRIPTION

The weight loss composition constituting the present invention is a purposefully formulated admixture comprising at least one amino acid able to serve as a precursor of catecholamine biosynthesis in-vivo; one or more sympathomimetic agents; a lipolytic agent; and a high-Dalton macromolecular protein. In addition, the formulated admixtures will optionally, but desirably, include at least one micronutrient.

This purposeful blending of different nutritional ingredients will act together and function in concert after being administered concurrently in-vivo to generate an enhanced physiological effect and cause a marked increase in the rate of basal metabolism for a living subject, an enhanced rate which is far greater than could be expected from the sum of each component ingredient when acting alone.

The weight loss composition is typically prepared as a purposefully formulated dry particle admixture; is subsequently modified into liquid or fluid form; and is intended to be orally swallowed and consumed by an obese person as a beverage. If desired, however, the purposely-formulated composition may be prepared as a thick syrup or as a semi-dry powder, which is to be constituted subsequently into a free-flowing fluid beverage form by the addition of water.

The formulated weight loss composition, after being orally ingested, is capable of performing a variety of different and multiple physiological functions in-vivo. These in-vivo functions include:

(i) increasing the person's basal metabolic rate;
(ii) enhancing the metabolism of body fat in a person by use of a formulated composition which is truly preferential for lipolysis and fat oxidation;
(iii) maintaining a low glycemic index for the individual;
(iv) preserving and replenishing lean muscle mass for the person;
(v) providing for dopaminergic (D2-receptor) brain stimulation, which in turn results in a greater cognitive function and in affective augmentation;
(vi) beneficially altering the individual's mood, attitude, and state of mind; and
(vii) causing a meaningful weight loss for the individual, while avoiding major adverse side effects.

I. The Underpinnings of the Present Invention

In order to understand properly and to appreciate fully what the present invention truly is, it is useful to identify and summarily review what constitutes its underlying bases and perspectives.

1. The ability to increase a person's basal metabolism rate or "BMR" by exciting the person's sympathetic nervous system and accelerating its activity is a well-established and long recognized event. Such stimulation typically occurs as a consequence of a person performing a physical act or engaging in a strenuous activity such as physical exercise over a sustained period of time. In the alternative, one can employ one or more pharmacologically active substances to effect a direct stimulation of the person's sympathetic nervous system in order to increase his basal metabolism rate.

For example, catecholamines and catecholaminergic stimulation are long known to be effective for increasing a person's basal metabolism rate by direct reaction with his sympathetic nervous system. It will be noted that, by definition, catecholamines are a specified and distinct class of chemical compounds, dihydroxyphenylalkylamines; are naturally found in the adrenal, medulla, neurons, and brain of the human body; and are normally synthesized in-vivo via a chain of biochemical reactions and pathways starting with its amino acid precursor, L-tyrosine.

Accordingly, under normal in-vivo conditions, the precursor amino acid L-tyrosine is hydroxylated to 3,4-dihydrophenylalanine (DOPA), which is then decarboxylated to form dopamine. Norepinephrine and epinephrine, the two other major catecholamines, are also generated in-vivo in a similar biosynthesis fashion; and these three biosynthesized catecholamines serve as different neurotransmitters and hormones within the living body.

2. The present invention fully recognizes the classical modes by which a person's basal metabolic rate can be increased within the living body; and carefully chooses to provide both an indirect stimulus produced in-vivo, as well as a direct biochemical stimulator, of the sympathetic nervous system—a two-pronged approach—to induce a marked increase in basal metabolic rate in-vivo.

The present invention therefore presents a carefully formulated weight loss composition that is unusually effective for accelerating a person's individual basal metabolic rate; and thereby concomitantly causes a substantive weight loss for the individual, while avoiding major adverse side effects. These functions and capabilities are provided by an unique combination of nutritional elements that act in concert, and which together produce a far greater overall result and beneficial effect than can be obtained by the additive sum of having each ingredient act independently.

3. The instant invention also is purposefully formulated to enhance the oxidative metabolism of a person's body fat; to preserve his lean muscle mass despite achieving an accelerated basal metabolic rate; and to amplify a person's mental cognition and elevate his frame of mind. Specific reactant ingredients are provided by the formulated composition (in addition to the direct and indirect stimulators of the sympathetic nervous system) to initiate and carry out all these highly desirable auxiliary functions in-vivo.

II. The Indirect and Direct Stimulators of the Sympathetic Nervous System in the Weight Loss Composition A. At Least One Amino Acid Able to Serve as a Pharmacologically Active Precursor in the Catecholamine Biosynthesis Pathways The present invention relies upon the in-vivo administration of at least one exogenous amino acid which will serve as a biologically active precursor compound and whose biochemical presence will initiate catecholamine biosynthesis in-vivo. These exogenous amino acid(s), best exemplified by L-tyrosine and L-phenylananine respectively, will cause a demonstrable increase in the production of the major catecholamines synthesized in-vivo via their well documented biosynthesis pathways; which, in turn, will stimulate and cause a pronounced increase in sympathetic nervous system activity; and which will then concomitantly induce an accelerated rate of basal metabolism for that individual.

Via this mechanism of action and in this indirect manner, the purposeful oral administration of one or more exogenous precursor amino acids will actively initiate an increased biosynthesis of catecholamines in-vivo, which will ultimately lead to and cause a substantive weight loss for that living subject.

At least one amino acid precursor compound is present in the prepared formulation; and the preferred precursor compounds are L-phenylalanine, L-tyrosine, or both in combination. Table 1 below gives an exemplary, but non-exhaustive, listing of suitable precursor amino acids.

TABLE 1

| Bioactive amino acid precursors of catecholamines |
| --- |
| L-tyrosine; |
| N-acetyl-L-tyrosine; |
| L-3-hydroxytyrosine; |
| L-phenylalanine; |
| 3-(3,4-dihydroxyphenyl)-L-alanine; |
| Methyl-3-(3,4-dihydroxyphenyl)-L-alanine; and |
| L-dopamine. |

It is also useful here to provide an illustrative range of the quantitative amounts or dosages for the chosen amino acid precursor compound(s) when employed as part of the prepared formulation. In its broadest range, each amino acid precursor compound can be employed in a quantity from about 10 mg to 10 g; while in a preferred range they appear in about 250 mg to 2,500 mg doses; and in the most preferred embodiments, they are present in quantities ranging from about 500 mg to 1,000 mg.

In the preferred embodiments, the composition of the present invention will employ two amino acid precursors, L-phenylalanine and L-tyrosine, together in combination. Once co-administered, L-phenylalanine and L-tyrosine will act in concert to stimulate catecholamine biosynthesis, cause a stimulation of the sympathetic autonomic nervous system, and induce an increase in basal metabolic rate and fatty acid oxidation.

A quantity of 1000 mg of L-phenylalanine is preferred, but as much as 10 g can be taken orally without deleterious side effects. L-Tyrosine when combined with L-phenylalanine at doses of 1000 mg or more has a mutual enhancing effect in sympathetic nervous stimulation without causing deleterious side effects. It will be noted also that the other known isomeric forms of phenylalanine and tyrosine, D-phenylalanine and D-tyrosine, are not biologically active and would provide no intrinsic physiologic benefit.

Oral administration of L-phenylalanine, in addition to triggering sympathetic nervous system stimulation, also independently will increase production of cholecystokinin, an endogenous hormone normally secreted by the small intestine—which is an event which then results in gallbladder contraction, and a release of bile into the small intestine for the emulsification of fat, and a simultaneous release of lipase enzymes by the pancreas. This enhanced release of cholecystokinin represents a corollary and auxiliary result that does not directly affect the person's basal metabolic rate.

B. One or More Exogenous Sympathomimetic Agents

The present invention also employs at least one agent for direct chemical stimulation of the sympathetic nervous system in order to cause a marked increase in basal metabolic rate in-vivo. These pharmacologically active compositions exist today as a diverse range of different chemical compounds; and are classified collectively herein by the term "exogenous sympathomimetic agents".

Most exogenous sympathomimetic agents are commonly available today from a variety of different commercial sources; can be obtained either as a naturally occurring substance or a chemically synthesized product; and have been frequently used for many different purposes both in the modern pharmaceutical industry as well as in traditional folk medicaments.

At least one exogenous sympathomimetic agent is present in each prepared formulation; and the preferred agents are caffeine, or ginseng, or both of these in combination. Table 2 below gives an illustrative, but non-exhaustive, listing of sympathomimetic agents.

TABLE 2

| Exogenous sympathomimetic agents |
|---|
| caffeine; |
| ephedrine; |
| methylphenidate; |
| synephrine; |
| nicotine; |
| *citrus aurantium*; |
| neroli oil; |
| guarana; |
| *ginseng*; |
| green tea extract; |
| epigallocatechin gallate; and |
| *rhodiola rosea*. |

It is also useful here to provide an illustrative range of quantitative amounts or dosages for the chosen sympathomimetic agent(s) when employed in the prepared formulation. However, because each agent is pharmacologically unrelated to another, these ranges will be represented herein by the preferred examples of caffeine and ginseng. Thus, in the broadest range, ginseng can be used in the range from about 50 mg to 2.7 g, and caffeine from about 5 mg to 1000 mg respectively; while in a preferred range ginseng is present from about 200 mg to 1500 mg, and caffeine from about 5 mg to 195 mg respectively; and in the most preferred embodiments ginseng is used in quantities from about 250 mg to 1000 mg, and caffeine from about 25 mg to 95 mg respectively.

In general however, most prepared formulations of the present invention will contain between 20 mg and 200 mg of caffeine; however, if desired, doses as large as 1,000 mg of caffeine can be comfortably tolerated. Nevertheless, an amount less than 195 mg of caffeine is most preferred because at doses over 200 mg the risk of incurring adverse cardiac side effects, such as cardiac arrhythmia, must be considered for susceptible patients.

Similarly, ginseng is an adaptogenic herb with effective and potent sympathomimetic properties, and thus ginseng can be utilized at dose amounts ranging between 200 mg and 2700 mg without risk of deleterious side effects. In general, a dose amount of 500 mg of ginseng is deemed to be most preferred.

C. The Unusual Value and Unexpected Benefit Provided by Co-Administering the Amino Acid Precursor and the Sympathomimetic Agent in Combination The Unforeseen Primary Effect In accordance with the purposeful formulation of the present invention, it must be noted and appreciated that the physiologic effect of administering one or more exogenous amino acids (such as L-phenylalanine and L-tyrosine) will be greatly augmented and enhanced by the concurrent administration of one or more exogenous sympathomimetic stimulants (such as caffeine and ginseng). In point of fact, when the sympathomimetic agents are co-administered together with the amino acid precursor(s) of catecholamine synthesis, a demonstrable and unforeseen quantum increase in pharmacological activity and physiological effect is generated in-vivo—i.e., a surprising rise in and acceleration of basal metabolic rate which far exceeds the expected sum effect of the individual potency for each of the two reactant ingredients when administered alone.

Thus, albeit for reasons which are not yet well understood presently, the co-administration of amino acid precursor compounds (which initiate the biosynthesis of catecholamines as indirect stimulators) concurrently with exogenous sympathomimetic agents (which act as direct stimulators) will generate an unforeseen mutual effect and produce an unpredictable combined result—a greatly enhanced increase in basal metabolic rate which quantitatively is far larger than that achievable by the sum additive effect obtained when using each of the two reactant ingredients individually and alone.

The Unexpected Secondary Benefit

This remarkable and hereto unknown achievement of generating such a quantum increase in basal metabolic rate (which is much greater than was previously available before) also offers another corresponding opportunity and provides a second major benefit and advantage for the present invention. The concurrent administration of these two different kinds of reactant ingredients allows the manufacturer of the weight loss composition to decrease and substantially diminish the true quantitative amount necessary for each dose of the amino acid precursor compound(s) and/or the sympathomimetic agent(s) in the prepared formulation. Thus the measured amounts of amino acid precursor compound(s) and/or the sympathomimetic agent(s) which were considered to be the minimal threshold dose necessary in order for each active substance to produce its desired physiological effect in-vivo is now considerably reduced and is quantitatively far less than was used before.

Therefore, because the invention purposefully co-administers sympathomimetic agents and amino acid precursor compounds together to create a uniquely enhanced stimulatory effect, the prepared formulation can employ substantially smaller dose amounts of one or both of these reactant ingredients to achieve the targeted goal of markedly increasing the person's basal metabolic rate. Therefore, the second unforeseen and unpredictable outcome is that, despite the reduction in the typical dosage quantity for each individual reactant ingredient when concurrently administered together, these substantially reduced quantities of amino acid precursor compound(s) and/or sympathomimetic agent(s) will nevertheless function together and act in concert to stimulate the sympathetic nervous system in-vivo. This result will, in turn, then subsequently cause the intended effect and outcome—a marked acceleration in the rate of basal metabolism for that individual.

III. The Other Component Substances Comprising the Weight Loss Composition

A. An Exogenous Lipolytic Agent

For purposes of properly appreciating the present invention, it will be noted that the person's native rates of lipolysis and fatty acid oxidation will become altered as the consequence of the body's newly increased biosynthesis of catecholamines in-vivo; and the larger production quantities of catecholamines then existing in-vivo will—of themselves—initiate and cause a sharp rise in the rate of fat metabolism.

Nevertheless, despite the initial increase in the rate of fatty acid oxidation caused by the larger production quantities of biosynthesized catecholamines, a further increase and substantially greater augmentation of the then existing rate for fatty acid oxidation will be created by a concurrent administration of at least one exogenous lipolytic agent such as L-carnitine (a compound long known as an "acyl carrier"). The inclusion and co-administration of a lipolytic agent in combination with the sympathomimetic stimulant(s) and the amino acid precursor compound(s) thus will substantially raise and further increase the current rates of fat metabolism and fatty acid oxidation to a uniquely elevated and amplified state.

Accordingly, to achieve the desired greater enhancement and additional increase in the rate of fatty acid oxidation and fat metabolism, at least one exogenous lipolytic agent is present as a reactant ingredient in the prepared formulation; and, for this purpose, the most preferred choice of lipolytic agent is L-carnitine. A number of other suitable lipolytic agents are also known and commonly available; and an exemplary, but non-exhaustive, listing of such exogenous lipolytic agents is provided by Table 3 below.

TABLE 3

| Exogenous lipolytic agents |
| --- |
| L-carnitine; |
| Acetyl-L-carnitine; |
| Sodium pyruvate; |
| Calcium pyruvate; and |
| Conjugated linoleic acid. |

It is also useful here to provide an illustrative range of dosages for the chosen lipolytic agent(s) when employed as part of the prepared formulation. However, because each lipolytic agent is pharmacologically unrelated to another, the dose ranges will be demonstrated and represented herein by the preferred example of L-carnitine. Thus, as illustrative of all lipolytic agents generally, L-carnitine can be used most broadly in amounts ranging from about 5 mg to 6 g; while in a preferred range L-carnitine is used in quantities from about 50 mg to 2,500 mg; and in the most preferred embodiments, L-carnitine is used in dosages ranging from about 250 mg to 1,500 mg.

In many preferred embodiments, the weight loss composition will comprise L-carnitine as the lipolytic agent of choice. L-carnitine is known to be an amino acid produced by hepatic and renal tissues and will facilitate fatty acid oxidative metabolism in-vivo. For these reasons, exogenous L carnitine is utilized as a preferred reactant ingredient in the prepared formulation, will aid in causing a rise in basal metabolic rate, and thus help promote a weight loss. In general, a dose quantity of 200 mg of L-carnitine is preferable, although amounts as high as 6 g can be clinically tolerated without incurring deleterious side effects. Please note, however, that the D-carnitine isomeric form is not biologically active and will provide no physiological benefits.

L-carnitine also can produce a secondary thermogenic effect as an ancillary benefit aside from further increasing the rate of basal metabolism. Some of the other benefits derived from use of L-carnitine include the capability to increase cardiac contractility and the heart rate.

B. A High-Dalton Macromolecular Protein

Another major feature of the present invention is that the preferred formulations employ one or more macromolecular proteins having a relatively high Dalton weight as an active ingredient and reactant. The presence and inclusion of a high-Dalton macromolecular protein is neither an incidental circumstance nor a merely fortuitous event. To the contrary, the weight loss composition in certain middle range formulations and in all its preferred embodiments intentionally comprises at least one kind of high-Dalton macromolecular protein for a specific purpose, which is: to enable the living body to avoid depleting existing skeletal muscles for their available protein stores—and thereby evade and escape from the pathological condition of "muscle wasting" where the body cannibalizes its own muscle proteins to produce enough energy. This pathological condition should be particularly avoided over the time duration when the person's basal metabolism rate has become markedly increased and his rates of lipolysis and fatty acid oxidation are also elevated and noticeably enhanced.

In its broadest definition, a high-Dalton protein is any protein, polypeptide, or oligopeptide having a molecular weight of about 1400 Daltons or more, regardless of its amino acid content, or its physical state, or its degree of structural integrity, or its source of origin, or the manner by which it is derived. In short, the sole essential criterion and requirement is met by its mass/weight, as conventionally measured in daltons.

However, as regards the present invention, a relatively new family of protein compositions, called macromolecular proteins, is highly desirable for use. Macromolecular proteins are naturally present in vegetables and milk; and typically are proteins that have been generated by enzyme reaction or acid digestion—a derivation and processing that creates and produces a purer, more metabolically active kind of protein product. Such enzymatically or acid generated proteins typically have atomic weights of 1400 Daltons or greater, and therefore are termed "macromolecular proteins".

Preferably, at least one high-Dalton macromolecular protein (regardless of its processing or source) is present in the prepared formulation; and one a preferred high-Dalton macromolecular protein is sold commercially as Actinase® protein products. In addition, an exemplary, but non-exhaustive, listing of other available high-Dalton macromolecular proteins is presented by Table 4 below.

TABLE 4

High-Dalton macromolecular proteins

Amicare ® digested proteins;
EZMix ® digested proteins;
Hy-Case ® protein products;
Actinase ® protein products;
N-Z-Amine ® digested proteins;
N-Z-Case ® digested proteins;
whey protein hydrolysate;
whey enzymatic protein hydrolysate;
soy protein acid hydrolysate;
casein acid hydrolysate, from bovine milk; and
casein enzymatic hydrolysate, from bovine milk.

It is also desirable here to provide an illustrative range of quantitative amounts or dosages for the chosen high-Dalton macromolecular protein when employed as part of the prepared formulation. However, because each macromolecular protein product is clearly different from any other, the generally acceptable dose amounts will be presented as a series of quantitative dry weight/mass ranges. Thus, in the broadest range, the chosen high-Dalton macromolecular protein will be used in an amount varying from about 1 g to 100 g; while in a preferred range, the macromolecular protein will be used in quantities from about 5 g to 25 g; and in the most preferred embodiments, the macromolecular protein is used in doses ranging from about 10 g to 15 g.

The physiologic effect and advantage of orally ingesting at least one high-Dalton macromolecular protein as part of the prepared formulation is a high rate and degree of protein absorption from the digestive tract of the living subject—i.e., a greatly increased protein bioavailability in comparison to that existing under typical circumstances. Then, after becoming rapidly absorbed by the cells lining the digestive tract, the bulk of these high-Dalton macromolecular proteins will be transported and stored in the living skeletal muscle cells of the body, rather than be degraded into substitute sources of energy.

It will be recognized also that the continuing bioavailability of and rate of uptake for high-Dalton macromolecular proteins is much greater than that for lower Dalton weight proteins (having a molecular weight less than about 1400 Daltons) and is also greatly facilitated in comparison to other kinds of proteins; and the continuing abundance and excess bioavailability of such high-Dalton macromolecular proteins will be used by the body systems to maintain existing muscle as well as to generate new muscle tissue.

Then, at such time as the preferred energy sources of the body are in short supply, and the body would then typically begin to deplete the skeletal muscles of protein for use as an alternative energy supply—the abundance of high-Dalton macromolecular proteins enables the body to avoid destroying its own muscular system. The continuing supply of high-Dalton macromolecular proteins provided by the ingested formulations are immediately available from the digestive tract for use as an alternative energy source; and this bioavailability in the digestive tract avoids depleting protein stores from muscle tissue, and thus prevents the "muscle wasting" that typically occurs with most fasting conditions.

The abundance and continuing bioavailability of high-Dalton macromolecular proteins also reduces the effect of creatinine toxicity on the person's kidneys (a very desirable and beneficial effect); and meaningfully increases the individual's rate for creatinine clearance as a reaction byproduct. Decreasing the breakdown rates for muscle also has added protective effects—by improving glucose tolerance, increasing insulin sensitivity, and producing a favorable glycemic index. In particular, the glycemic index is very low for those individuals who are diabetics and/or glucose-intolerant.

There are also several other reasons for using high-Dalton macromolecular proteins in the prepared formulations. These include: (a) high-Dalton macromolecular proteins are miscible in water and can be utilized in fluids and beverages, unlike low-Dalton proteins which can only be used as solid powders and in suspensions; (b) less biodegradable low Dalton proteins are typically converted into glucose, thereby actually increasing the person's glycemic index; and (c) high-Dalton macromolecular proteins are preferentially stored in living muscle, thus lowering the person's glycemic index.

Accordingly, the concurrent administration of high-Dalton macromolecular proteins—in combination with the amino acid precursor compound(s), the sympathomimetic agent(s), and desirably a lipolytic agent—will prevent the muscle wasting that typically occurs in the human body under most fasting conditions or controlled dietary regimens. The concurrent introduction and in-vivo presence of high-Dalton macromolecular proteins is thus most beneficial in that it will offer the body an alternative source of available proteins, and concomitantly also provide a continuous cycle of lean muscle replenishment and a low glycemic index.

C. At Least One Micronutrient

Another result of an increase in the rate of metabolism, particularly with the oxidation of fat, is the production of destructive free radicals. To negate such harmful effects, it is desirable to include at least one antioxidant within the weight loss composition that will react readily with free radicals and neutralize/destroy them before they can seriously damage the body tissues.

The weight loss composition comprising the present invention will therefore desirably include one or more micronutrient substances as entirely optional, but desirable auxiliary aids for facilitating lipolysis and fat metabolism. Preferably, at least one micronutrient is present in the prepared formulation; and the chosen micronutrients will desirably include various B-complex vitamins and an antioxidant, such as vitamin C, to scavenge free radicals produced by oxidative metabolism.

To demonstrate the range and variety of available micronutrients that are suitable for use in the present invention, an exemplary, but non-exhaustive, listing is given by Table 5 below.

TABLE 5

Micronutrients boron citrate;
calcium citrate;
chromium nicotinate;
chromium picolinate;
copper gluconate;
magnesium citrate;
manganese citrate;
methylsulfonylmethane;
potassium citrate;
L-selenomethionine;
zinc citrate;
para-aminobenzoic acid;
phosphatidyl choline;
piperine;
rutin;
tocotrienols;
thiamine;
riboflavin;
niacinamide;
niacin;
L-proline;
alpha-lipoic acid;
choline chloride;
indium sulfate;
lithium carbonate;
potassium iodide;
rubidium chloride;
sodium molybdate;
sodium tungstate;
strontium chloride;
beta carotene;
biotin;
folic acid;
inositol;
lutein;
calcium pantothenate;
pyridoxine hydrochloride;
cyanocobalamin;
calcium ascorbate.
cholecaliferol;
alpha-tocopherol succinate;
L-carnosine;
L-glutathione; and
L-methionine.

It is not useful here to provide an illustrative range of dosages for the each of the chosen micronutrient(s) when employed as part of the prepared formulation—primarily because each micronutrient is pharmacologically unrelated to any other. Nevertheless, because each micronutrient is conventionally known and the generally beneficial dose ranges are commonly used and routinely available, this information is deemed to be available on demand from the public domain.

In many preferred embodiments, the weight loss composition will comprise vitamin C, or ascorbic acid, as an antioxidant. A quantity of 150 mg of vitamin C is preferable, although higher doses can be clinically tolerated without deleterious side effects. However, larger quantities of vitamin C can adversely affect the taste, or tartness, of the beverage to the consumer. It will be recalled also that Vitamin C is not stored in body tissues and is rapidly eliminated following oral administration, thereby preventing any potential toxicity.

The weight loss composition will also desirably include the B-complex vitamins, and is not limited to the use of B1, B2, B3, B5, B6, B9, B12, and biotin. A quantity of 500% of the USDA Recommended Daily Allowance (RDA) is preferable, although higher doses can be clinically tolerated without deleterious side effects. Vitamin B is not stored in body tissues and is rapidly eliminated following oral administration, preventing potential toxicity.

IV. Exemplary Prepared Formulations

A. The Minimalist Formulations

A variety of minimally formulated dry admixtures can be prepared in advance, stored indefinitely, and then combined with a liquid aqueous carrier to form a fluid beverage. These minimalist compositions are patterned upon a single formulation basis, which is a dry admixture comprising:
(i) at least one exogenous amino acid precursor able to be utilized in a catecholamine biosynthesis pathway;
(ii) at least one exogenous sympathomimetic agent able to stimulate the sympathetic nervous system; and
(iii) at least one substance selected from the group consisting of a lipolytic agent and a high-Dalton macromolecular protein.

Thus, two different general types of purposefully formulated minimal dry admixtures can be prepared. For illustrative purposes only, by employing the same preferred choices shared in common for each type, the two type-representative examples are as follows.
Minimalist Type Example A
hydrolyzed macromolecular protein (1 g-100 g),
L-tyrosine (10 mg-10 g), and
ginseng (50 mg-2.7 g).
Minimalist Type Example B
hydrolyzed macromolecular protein (1 g-100 g),
L-tyrosine (10 mg-10 g), and
L-carnitine (5 mg-6 g).

B. The Middle Range of Formulations

A far greater range and variety of middle range of particle formulations can be prepared in advance, stored indefinitely, and then combined at will with a liquid aqueous carrier to form a fluid beverage. These middle range compositions are also patterned upon a single formulation basis, which is a dry admixture comprising:
(i) at least one exogenous amino acid precursor able to be utilized in a catecholamine biosynthesis pathway;
(ii) at least one exogenous sympathomimetic agent able to stimulate the sympathetic nervous system; and
(iii) a lipolytic agent; and
(iv) a high-Dalton macromolecular protein.

Thus, a far larger variety of purposefully formulated middle range dry admixtures can be prepared based on the four reactant ingredient pattern. Again for illustrative purposes only, by employing the same preferred choices of ingredients as used above, the variety and range of representative examples is demonstrated as follows.
Middle Range Example C
hydrolyzed macromolecular protein (1 g-100 g),
L-tyrosine (10 mg-10 g),
ginseng (50 mg-2.7 g), and
L-carnitine (5 mg-6 g).

C. The Preferred Formulations

In its preferred formats, the weight loss composition will include one or more amino acids which is a pharmacologically active precursor in the catecholamine biosynthesis pathway; one or more sympathomimetic agents; a lipolytic agent, a high-Dalton macromolecular protein; and micronutrients. These reactant ingredients are combined as a dry particle mixture and made into a prepared beverage fluid on-demand. The formulations are specifically adapted to perform multiple physiologic functions: weight loss preferential to lipolysis or fat metabolism, low glycemic index lean muscle replenishment, and dopaminergic (D2-receptor) brain stimulation resulting in cognitive and affective augmentation as a secondary byproduct of increasing the basal metabolic rate. Several illustrative and representative examples of preferred formulations are given below.

PREFERRED EXAMPLE 1

A Typical Composition

A typical dry formulation will be an admixture of ingredients, and will include all of the following: hydrolyzed macromolecular protein (12.5 g), L-tyrosine (1000 mg), L-phenylalanine (1000 mg), ginseng (500 mg), caffeine (40 mg), L-carnitine (200 mg), ascorbic acid (150 mg), thiamine (7.5 mg), riboflavin (7.5 mg), niacin (100 mg), pantothenic acid (50 mg), pyridoxine (10 mg), folic acid (0.5 mg), cobalamin (0.2 mg), and biotin (1 mg).

PREFERRED EXAMPLE 2

A Cold Weather Composition Formulation

A cold weather formulation will typically include all of the following: Hydrolyzed macromolecular protein (12.5 g), L-tyrosine (1000 mg), L phenylalanine (1000 mg), ginseng (500 mg), caffeine (40 mg), L-carnitine (200 mg), capsaicin (1 mg), ascorbic acid (150 mg), thiamine (7.5 mg), riboflavin (7.5 mg), niacin (100 mg), pantothenic acid (50 mg), pyridoxine (10 mg), folic acid (0.5 mg), cobalamin (0.2 mg), and biotin (1 mg).

PREFERRED EXAMPLE 3

A Caffeine-Free Composition Formulation

On many use occasions, a caffeine-free formulation is most desirable and will include: Hydrolyzed macromolecular protein (12.5 g), L-tyrosine (1000 mg), L-phenylalanine (1000 mg), ginseng (500 mg), L-carnitine (200 mg), ascorbic acid (150 mg), thiamine (7.5 mg), riboflavin (7.5 mg), niacin (100 mg), pantothenic acid (50 mg), pyridoxine (10 mg), folic acid (0.5 mg), cobalamin (0.2 mg), and biotin (1 mg).

V. The Conversion of the Dry Reactant Ingredients Into Fluid Form

The weight loss compositions may be manufactured and sold as a ready-to-drink beverage for immediate consumption by the person. In the alternative, the formulated compositions may be prepared as syrup concentrates or semi-dry powders, which are to be converted as desired into fluid form by the addition of water or a liquid aqueous based carrier. Such conversion of the syrup or semi-dry admixtures into fluid form is made using sufficient quantities of water (or another aqueous based liquid) to ensure that the beverage about to be ingested contains the active components in the proper proportions and percentages as previously stated herein. Alternatively, the weight loss composition can be housed in a specially designed container suitable as a beverage delivery system or kit.

A. The Liquid Carrier

The dry weight loss composition may be prepared by simply admixing the appropriate reactant ingredients and packaging them in conventional beverage containers used for such purposes. The liquid carrier used on-demand to form the fluid beverage may be distilled, deionized, carbonated, or mineral water; and the liquid will typically also contain a small amount of non-glucose or low glycemic index sweetener (such as aspartame or sucralose) to impart a pleasant sweet taste to the prepared beverage. Such a fluid beverage will have a total caloric load not to exceed 60 kcal per serving, and favored with one or more natural and artificial sweeteners, either individually or in combination, in their usual proportions. The resulting fluid beverage will be initially preserved by pasteurization or cold sterilization; and is intended to be drank at an average volume intake of less than one liter per day.

Alternatively, the dry admixed reactant ingredients of the chosen formulation can be mixed at will with a very small amount of water (such as less than 30 ml) to produce a thick syrup which will later be diluted to provide multiple units in the proper dose amounts; or will be poured into capsule form, designed for optimum portability in situations requiring little weight or baggage.

In addition, the weight loss composition may be kept as a dry powder mixture for an indefinite time period without degradation. Then, at a chosen later time, the dry powder will be combined with water (or another aqueous based liquid), and desirably also with a small amount of non-glucose or low glycemic index sweetener such as aspartame or sucralose) to impart a pleasant sweet taste for the beverage. In its preferred forms, the beverage will have a total caloric value not to exceed 60 kcal per serving, after being properly constituted as a ready to drink fluid.

Optionally, the dry particle admixture may be flavored with one or more natural and artificial sweeteners, either individually or in combination, in their usual proportions. The powder can then be packaged in individual moisture and tamper-resistant packaging available commercially for such purposes. The compressed dry powder mixture (or equivalent solid forms with the same composition) is intended for a daily intake of 3 units or less. These concentrations are merely indicative of what can be commonly done, and more concentrated beverages can be prepared on a similar formula basis.

The weight loss composition may be consumed before meals to reduce caloric consumption during meals, or after meals to reduce eating between meals, or consumed in lieu of one or more traditional meals.

B. Optional Flavorings, Colors, and Thermogenic Agents

One or more natural or artificial flavors may be added to the fluid, preferably yielding 8 fluid ounces of total beverage. The constituted beverages also may contain citric acid, one or more nature of artificial food dyes and colors, and sodium benzoate as a preservative—each for its usual purpose.

The fluid weight loss composition can optionally include a sweetening agent. The sweetening agent comprises any sweetening material conventionally used in commercial beverages and in their usual concentrations. Examples include, but are not limited to, sweeteners with a low glycemic index, such as aspartame and sucralose.

The beverage also may contain various organic acids, such as citric acid; one or more natural or artificial flavors; one or more preservatives; food colors and dyes; and the like, in their usual proportions.

The weight loss composition can also optionally include capsaicin and piperine as thermogenic agents, in their usual quantities, to yield a beverage composition suitable for anyone exposed to below-normal weather conditions and/or extreme cold—such as those persons living in cold weather climates and extreme weather conditions; factory workers, armed forces personnel, police, firemen, and aircraft ground crews; and those persons enjoying winter recreational activities such as skiing, snow boarding, and ice-skating.

C. Packaging

The packing of the weight loss compositions may take any variety of forms. For instance, the product may be manufactured and sold as a ready-to-drink beverage for immediate consumption. Alternatively, the weight loss compositions may be prepared in concentrated or powder form that is to be later constituted for use by the addition of water or another liquid. Such conversion will be made using the appropriate amounts of water or other liquid to ensure that the beverage about to be ingested contains the active components in their proper proportions.

It will also be evident that the amount of water, or other liquid, to be added to the particle admixture is that volume required to provide the proper concentration of the active components for the size of the container for the beverage. Normally, such beverages, as with other drinks, come in a container holding at least 8 fluid ounces of the beverage.

The beverages are prepared by simply admixing the ingredients and packaging them in suitable containers or receptacles for such purposes. The beverage also may be contained in a specially designed receptacle as part of a beverage delivery system, or kit, adapted for oral consumption.

VI. Added Benefits and Advantages

Cognitive function and affective augmentation is an additional ancillary benefit which is obtained by stimulating the sympathetic nervous system. Dopamine is produced as a product via the catecholamine biosynthesis pathways and this results in a secondary, but physiologically significant, effect of causing dopaminergic (D2) receptor stimulation in the brain. This event leads to an improved cognitive function, an enhanced affective performance, and an increase in mental activity. Increasing dopamine levels in the brain also stimulates autonomic and motor functions indirectly by inducing a positive mood and a somewhat euphoric state of mind. Consequently, the individual is inclined to be more active and sociable.

Furthermore, an increase in mental stimulation alone has been shown to increase basal metabolic rate, independently from increased motor function and energy expenditure. Therefore, the stimulation of D2-receptors in the brain will concomitantly produce the secondary effect and result of increasing a person's basal metabolic rate.

VII. Empirical Experiments and Resulting Data

To demonstrate the merits and value of the present invention, a variety of anecdotal facts and experimental data are presented below. It will be expressly understood, however, that the facts and data provided below are merely the best evidence of the subject matter as a whole which is the present invention; and that the facts and data, while limited in content, are merely illustrative of the true breadth and scope for the present invention as envisioned and claimed.

The Experimental Trial

The Prepared Formulation

The weight loss composition experimentally evaluated was prepared as a typical preferred formulation described previously herein, and contained the following ingredients: hydrolyzed macromolecular protein (12.5 g); L-tyrosine (1000 mg); L-phenylalanine (1000 mg); ginseng (500 mg); caffeine (40 mg); L-carnitine (500 mg); and micronutrients (prescribed at 500% of USDA recommended daily allowance), including calcium ascorbate (150 mg), thiamine (7.5 mg), riboflavin (7.5 mg), niacin (100 mg), calcium pantothenate (50 mg), pyridoxine hydrochloride (10 mg), folic acid (0.5 mg), cyanocobalamin (0.2 mg), and biotin (1 mg).

Test Parameters

This specifically formulated weight loss composition was empirically evaluated with regard to its pharmacological and physiological effects on the basal metabolic rate using normal, healthy adult subjects. The test subjects were encouraged to maintain a log of their experience in the form of a daily journal.

The duration of the experimental non-randomized study was 10 to 12 calendar weeks. Specifically, the test subjects were four volunteers, male and female human adults, aged 26 through 67 years respectively. A pregnancy declination was required in female subjects of childbearing age.

The four test subjects were initially screened to meet the following clinical criteria:
(1) a normal body mass index of 25 or less;
(2) no cardiac risk factors (i.e., hypertension, diabetes mellitus, hyperlipidemia, or smoking);
(3) a maintenance of normal daily caloric intake of 1800 kcal or greater; and
(4) a cessation of carbonated beverages, coffee, and teas (all containing caffeine) through the duration of the study.

The initial baseline evaluation also included a measurement of the weight of each test subject as well as a measurement of percentage body fat as determined by a Lunar® DPX-IQ dual photon total body densitometry unit.

Following the initial baseline evaluation, all four test subjects were orally administered the formulated weight loss composition as an 6-ounce prepared beverage, which was ingested twice daily between meals. The administration of the beverage thus was an addition and supplement to their normal daily dietary intake of food and drink of their own choosing.

Subject Reactions

After beginning the test routine and routinely drinking the beverage twice per day, the four test subjects described a mild thermogenic effect (characterized as an increased mild perspiration), generally within four weeks. This thermogenic body reaction was attributed to an increase in the basal metabolic rate.

The test subjects also generally described a temporary euphoria effect, usually lasting between 3 to 6 hours, which consistently followed ingestion of the beverage. No adverse effects, however, were reported by the test subjects—including the absence of cardiac side effects such as palpitations, shortness of breath, or chest pain.

The test subjects also described feeling more slender and leaner, but at the same time reported feeling more alert and having more energy than before. The test subjects also reported qualitative improvement in muscular definition at the conclusion of the study.

Empirical Data and Results

A follow-up evaluation of the four test subjects after 10 to 12 weeks consumption of the weight loss composition showed an average weight loss of 5.5% of total body weight, and an average quantitative total body fat reduction of 2.2%, as determined by dual photon densitometry.

In addition, a major reduction of total body fat content—from 13% initially to 9% at test's end—was observed in a single male test subject. The remaining subjects showed an average total body fat reduction of 1.6%.

Overall, the empirical data showed a positive weight reduction and a meaningful loss of body fat composition by quantitative assessment—thereby confirming that a marked increase in basal metabolic rate was obtained using a prescribed oral dose of the weight loss composition ingested twice daily between normal meals.

VIII. Intended Users and Consumers

1. The benefits and advantages of the instant invention are largely evident from the foregoing description. For prolonged and permanent weight loss, particularly for obese persons, the weight loss composition constituting the instant invention must be orally ingested on a routine schedule and a regular basis in order to induce a continuous state of increased basal metabolic rate for the individual. It is also evident that the quantity and frequency of administration of the weight loss beverage will greatly influence the degree of increase in the relative rate of basal metabolism, and thereby control the degree of actual weight loss for the person. It is also expected that the amounts of weight loss beverage consumed to obtain an optimal or desired degree of weight loss will be highly variable; and similar or identical intake quantities of the weight loss beverage may not yield the same results because of the pharmacological variances and physiological differences existing among individual persons.

2. Obese patients, owing to their increased body mass index and propensity for having a lower than average basal metabolic rate, may require ingesting substantially larger quantities of the formulated weight loss beverage per day or over a longer time duration in order to obtain a comparable degree of weight loss in comparison to more lean subjects (as determined by the reduction of percentage body fat or the actual weight loss). A similar circumstance can also be expected in those human subjects taking β-adrenergic blocking medications—i.e., drugs which produce a blunted or attenuated response to sympathetic nervous stimulation.

The present invention is not to be limited in scope nor to be restricted in form, except by the claims appended hereto.

What is claimed is:

1. A dry weight loss composition suitable for ingestion by an obese subject, said composition comprising a particle admixture of:

at least one exogenous amino acid precursor able to be utilized in a catecholamine biosynthesis pathway, in a quantity within the range of 0.01 g to 1.0 g;

at least one exogenous sympathomimetic agent able to stimulate the sympathetic nervous system, in a quantity within the range of 0.2 g to 1.0 g;

a lipolytic agent able to increase and substantially augment the rate of fatty acid oxidation then existing in the obese subject, in a quantity within the range of 0.05 g to 1.0 g; and a high-Dalton macromolecular protein selected from the group consisting of proteins generated by enzyme reaction or acid digestion and having an atomic weight of not less than 1400 Daltons, said high-Dalton macromolecular protein enables the obese subject to avoid depleting skeletal muscles for their available protein stores in-vivo, in a quantity within the range of 1.0 g to 12.5 g.

2. A dry weight loss composition suitable for ingestion by an obese subject, said composition comprising a particle admixture of:

at least one exogenous amino acid precursor able to be utilized in a catecholamine biosynthesis pathway, in a quantity within the range of 0.01 g to 1.0 g;

at least one exogenous sympathomimetic agent able to stimulate the sympathetic nervous system, in a quantity within the range of 0.2 g to 1.0 g;

a lipolytic agent able to increase and substantially augment the rate of fatty acid oxidation then existing in the obese subject, in a quantity within the range of 0.05 g to 1.0 g;

a high-Dalton macromolecular protein selected from the group consisting of proteins generated by enzyme reaction or acid digestion and having an atomic weight of not less than 1400 Daltons, said high-Dalton macromolecular protein enables the obese subject to avoid depleting skeletal muscles for their available protein stores in-vivo, in a quantity within the range of 1.0 g to 12.5 g; and at least one micronutrient that reacts with free radicals in-vivo.

3. The dry weight loss composition as recited in claim 1 or 2 wherein said amino acid precursor is selected from the group consisting of L-tyrosine, N-acetyl-L-tyrosine, L-3-hydroxytyrosine, L-phenylalanine, 3-(3,4-dihydroxyphenyl)-L-alanine, methyl-3-(3,4-dihydroxyphenyl)-L-alanine, and L-dopamine.

4. The dry weight loss composition as recited in claim 1 or 2 wherein said sympathomimetic agent is selected from the group consisting of caffeine, ephedrine, methylphenidate, synephrine, nicotine, citrus aurantium, neroli oil, guarana, ginseng, green tea extract, epigallocatechin gallate, and rhodiola rosea.

5. The dry weight loss composition as recited in claim 1 or 2 wherein said lipolytic agent is selected from the group consisting of L-carnitine, acetyl-L-carnitine, sodium pyruvate, calcium pyruvate, and conjugated linoleic acid.

6. The dry weight loss composition as recited in claim 1 or 2 wherein said high-Dalton macromolecular protein is selected from the group consisting of soy protein enzymatic hydrolysate, soy protein acid hydrolysate, casein acid hydrolysate from bovine milk, and casein enzymatic hydrolysate from bovine milk.

7. The dry weight loss composition as recited in claim 2 wherein said micronutrient is selected from the group consisting of boron citrate, calcium citrate, chromium nicotinate, chromium picolinate, copper gluconate, magnesium citrate, manganese citrate, methylsulfonylmethane, potassium citrate, L-selenomethionine, zinc citrate, para-aminobenzoic acid, phosphatidyl choline, piperine, rutin, tocotrienols, thiamine, riboflavin, niacinamide, niacin, L-proline, alpha-lipoic acid, choline chloride, indium sulfate, lithium carbonate, potassium iodide, rubidium chloride, sodium molybdate, sodium tungstate, strontium chloride, beta carotene, biotin, folic acid, inositol, lutein, calcium pantothenate, pyridoxine hydrochloride, cyanocobalamin, calcium ascorbate, cholecalciferol, alpha-tocopherol succinate, L-carnosine, L-glutathione, and L-methionine.

* * * * *

UNITED STATES PATENT AND TRADEMARK OFFICE
CERTIFICATE OF CORRECTION

| | | |
|---|---|---|
| PATENT NO. | : 7,989,007 B2 | Page 1 of 1 |
| APPLICATION NO. | : 12/120223 | |
| DATED | : August 2, 2011 | |
| INVENTOR(S) | : Vincent Giuliano et al. | |

It is certified that error appears in the above-identified patent and that said Letters Patent is hereby corrected as shown below:

On the Title Page, in Item (56), under (Other Publications), in column 2, line 18, delete "Shakel,"" and insert -- Shake," --, therefor.

In column 4, line 14, delete "subutramine," and insert -- sibutramine, --, therefor.

In column 5, line 67, delete "trysin" and insert -- trypsin --, therefor.

In column 6, line 14, delete "steriod" and insert -- steroid --, therefor.

In column 7, line 41, delete "garncinia" and insert -- garcinia --, therefor.

In column 7, line 45, delete "camborgia" and insert -- cambogia --, therefor.

In column 10, line 37, delete "L-phenylananine" and insert -- L-phenylalanine --, therefor.

In column 17, line 48, delete "cholecaliferol;" and insert -- cholecalciferol; --, therefor.

In column 19, line 42, delete "folio acid" and insert -- folic acid --, therefor.

In column 22, line 21, delete "micronutients" and insert -- micronutrients --, therefor.

Signed and Sealed this
Twenty-fifth Day of October, 2011

David J. Kappos
*Director of the United States Patent and Trademark Office*